United States Patent
Yang et al.

(10) Patent No.: US 7,608,247 B2
(45) Date of Patent: Oct. 27, 2009

(54) USE OF OUTER MEMBRANE PROTEIN A IN TREATMENT/PREVENTION/DIAGNOSIS OF BACTERIAL INFECTION IN CENTRAL NERVOUS SYSTEM AND/OR PERIPHERAL BLOOD CIRCULATION

(75) Inventors: Yi-Yuan Yang, Taipei (TW);
Hsueh-Hsia Wu, Taipei (TW); Sy-Jye Leu, Taipei (TW); I-Jen Huang, Tainan County (TW); Neng-Yao Shih, Taipei (TW); Ko-Jiunn Liu, Taipei (TW); Mei-Ru Chen, Taipei (TW); Wen-Shyang Hsieh, Taipei (TW); Chi-Hsin Lee, Taipei (TW)

(73) Assignee: Taipei Medical University, Taipei City (TW)

( * ) Notice: Subject to any disclaimer, the term of this patent is extended or adjusted under 35 U.S.C. 154(b) by 0 days.

(21) Appl. No.: 12/046,165

(22) Filed: Mar. 11, 2008

(65) Prior Publication Data

US 2009/0233853 A1      Sep. 17, 2009

(51) Int. Cl.
*A61K 49/00*   (2006.01)
*A61K 39/108*  (2006.01)
*A61K 39/02*   (2006.01)

(52) U.S. Cl. .............. 424/9.2; 424/9.1; 424/130.1; 424/150.1; 424/163.1; 424/164.1; 424/184.1; 424/234.1; 424/257.1; 424/258.1; 424/259.1

(58) Field of Classification Search .............. 424/9.1, 424/9.2, 130.1, 150.1, 163.1, 164.1, 184.1, 424/234.1, 257.1, 258.1, 259.1
See application file for complete search history.

(56) References Cited

FOREIGN PATENT DOCUMENTS

WO    WO/93/25845    12/1993

OTHER PUBLICATIONS

Wertz, J.E., et al. A molecular phylogeny of enteric bacteria and implications for a bacterial species concept. J. Evol. Biol., vol. 16, pp. 1236-1248, 2003.*

* cited by examiner

*Primary Examiner*—Rodney P. Swartz
(74) *Attorney, Agent, or Firm*—WPAT, P.C.; Anthony King; Kay Yang

(57) ABSTRACT

The present invention provides a method for the treatment and/or prevention of bacterial infection in central nervous system and/or peripheral blood circulation in a mammal by administering effective amount of outer membrane protein A (OmpA) or its derivatives to a mammal. Also provided is an antibody binding to OmpA that can assay OmpA levels in a biological sample and detect or diagnose bacterial infection in central nervous system and/or peripheral blood circulation.

12 Claims, 7 Drawing Sheets

USE OF OUTER MEMBRANE PROTEIN A IN TREATMENT/PREVENTION/DIAGNOSIS OF BACTERIAL INFECTION IN CENTRAL NERVOUS SYSTEM AND/OR PERIPHERAL BLOOD CIRCULATION

FIELD OF THE INVENTION

The present invention is directed to a method for the treatment and/or prevention and/or diagnosis of bacterial infection in central nervous system and/or peripheral blood circulation in a mammal by administering an effective amount of outer membrane protein A or its derivatives to a mammal.

BACKGROUND OF THE INVENTION

In general, the central nervous system (CNS) is well defended against infection. The spine and brain are sheathed in tough, protective membranes. The outermost membrane, the dura mater, and the next layer, the arachnoid, entirely encase the brain and spinal cord. However, these defenses are not absolute. In some cases, bacteria gain access to areas within the CNS. Bacterial infections can be pyogenic infections (e.g., meningitis; brain abscess; subdural and epidural abscesses), tuberculosis, neurosyphilis, or leprosy. Typically, bacterial invasion results from the spread of a nearby infection; for example, a chronic sinus or middle ear infection can extend beyond its initial site. Bacteria may also be conveyed to the CNS from distant sites of infection by the bloodstream. In rare cases, head trauma or surgical procedures may introduce bacteria directly into the CNS. However, the source of infection cannot always be identified.

The goal of treatment of a bacterial infection is to stop the infection, relieve symptoms, prevent complications, and, if necessary, provide life support. A two-pronged approach is taken to treat bacterial infections. First, antibiotic therapy against an array of potential infectious bacteria is begun. The second stage involves surgery to drain the infected site. Once the bacterial species is identified, drug therapy can be altered to a more specific antibiotic. However, surgery may not be an option in some cases, such as when there are numerous sites of infection or when infection is located in an inaccessible area of the brain.

Outer membrane protein A (OmpA) was initially described by Henning and coworkers in 1975. It has 325 amino acid residues and exhibits heat-modifiable electrophoretic mobility on SDS-PAGE. The N-terminal domain of OmpA is comprised of 177 amino acids and is believed to traverse the outer membrane eight times. OmpA is involved in maintaining the shape of bacteria, serves as a phage receptor and a receptor for F-mediated conjugation, and has limited pore-forming properties. OmpA enhances uptake of LPS into macrophages and has been reported to be involved in *E. coli* invasion of the central nervous system. WO 9201001 provides a method for producing pure cloned outer membrane proteins, and to provide a method for their renaturation so as to regain biologically or immunologically active epitopes which are capable of eliciting the production of antibodies in animals.

However, there are no reports relating to the new use of an outer membrane protein A and its derivatives in the treatment and/or prevention and/or diagnosis of bacterial infection in central nervous system and/or peripheral blood circulation.

SUMMARY OF THE INVENTION

An object of the invention is to provide a method for the treatment and/or prevention of bacterial infection in central nervous system and/or peripheral blood circulation in a mammal, which comprises administering to said mammal an effective amount of an outer membrane protein A or its derivatives.

Another object of the invention is to provide a method for vaccinating a mammal to produce an antibody against bacterial infection in central nervous system and/or peripheral blood circulation, which comprises administering to said mammal an effective amount of an outer membrane protein A or its derivatives.

A further object of the invention is to provide a method of detecting or diagnosing bacterial infections in central nervous system and/or peripheral blood circulation in a mammal, which comprises coating a first specific anti-OmpA antibody onto a matrix surface that can immunospecifically bind to OmpA molecule in blood or OmpA on bacterial membrane, adding a sample from peripheral blood circulation and/or the central nervous system to the matrix, adding a second anti-OmpA antibody with a label, and detecting the binding of the anti-OmpA antibodies to the OmpA molecule or OmpA on bacterial membrane, wherein the binding result indicates that the mammal may suffer from the bacterial infections in the peripheral blood circulation and/or the central nervous system.

DETAILED DESCRIPTION OF THE INVENTION

Figure 1:
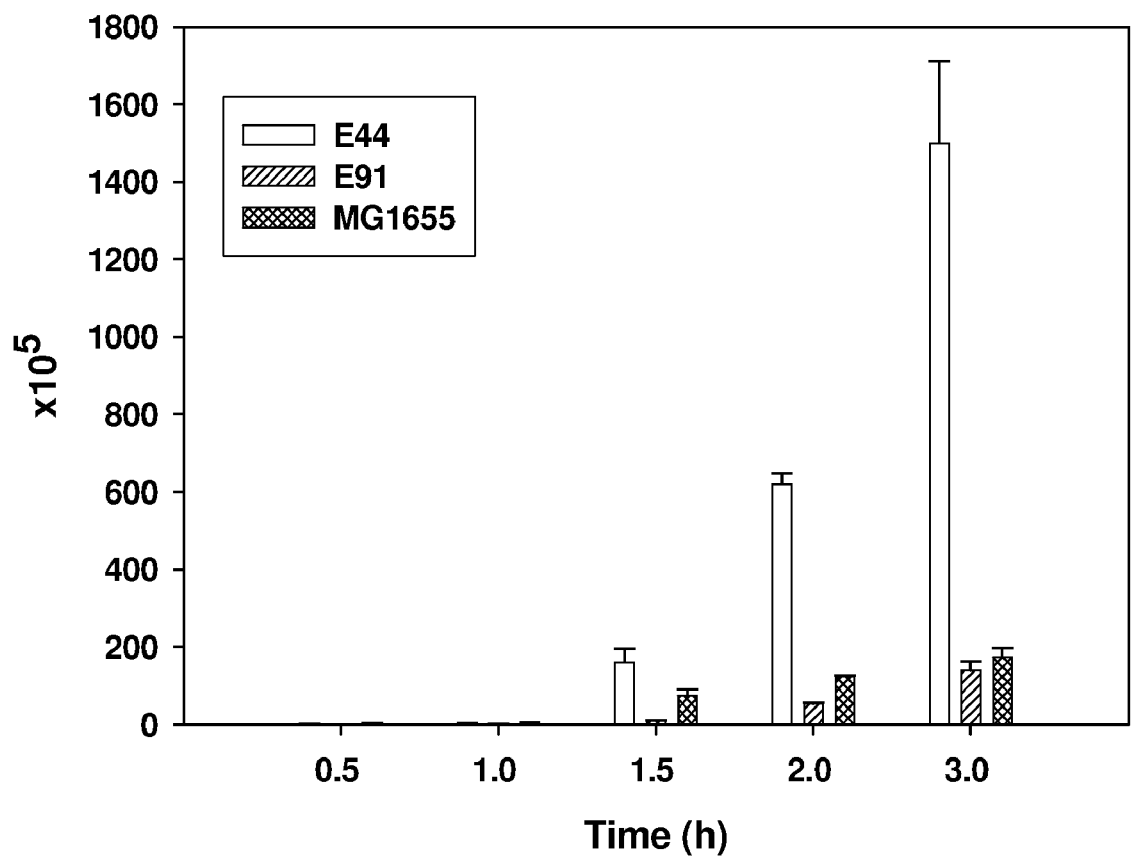
FIG. 1 shows the time course of *E. coli* strain adhesion.

The invention unexpectedly found that the outer membrane protein A (OmpA) can be used to treat and/or prevent and/or diagnose bacterial infection in central nervous system and/or peripheral blood circulation. In addition, an antibody binding to OmpA has been developed to assay OmpA levels in a biological sample and to detect or diagnose bacterial infection in central nervous system and/or peripheral blood circulation.

The invention provides a method for the treatment and/or prevention of bacterial infection in central nervous system and/or peripheral blood circulation in a mammal, which comprises administering to said mammal an effective amount of an outer membrane protein A or its derivatives.

The "central nervous system" used herein denotes to that part of the nervous system that consists of the brain and spinal cord. The "peripheral blood circulation" denotes to the blood in the systemic circulation.

The "bacterial infection" used herein denotes the infection caused by Gram-negative bacteria. Preferably, the bacterial infection is caused by *Enterobactereaceae* or other Gram-negative bacteria. More preferably, the bacterial infection is caused by *Shigella, Salmonella, Klebsiella, Escherichia, Citrobacter* or *Enterobactor*. Most preferably, the bacterial infection is caused by *Escherichia coli*.

The "outer membrane protein A (OmpA)" used herein denotes to any OmpA from Gram-negative bacteria and any recombinant OmpA. OmpA is an abundant structural protein of the outer membrane of Gram-negative bacteria. The "OmpA derivatives" denotes to proteins derived from OmpA, which have same function as that of OmpA. For example, OmpA recombinants having same function with OmpA are OmpA derivatives. Preferably, OmpA or its derivative is obtained from *Enterobactereaceae* or other Gram-negative bacteria. More preferably, OmpA or its derivative is obtained from *Shigella, Salmonella, Klebsiella, Escherichia, Citrobacter* or *Enterobactor*. Most preferably, OmpA or its derivative is obtained from *Escherichia coli*.

According to the invention, a therapeutically effective amount of OmpA or its derivatives of the invention can be administered to a mammal, including a human or non-human mammal, suffering from bacterial infection in both central nervous system and/or peripheral blood system. According to the invention, the administration of OmpA or its derivatives of the invention can be carried out in various ordinary ways. Administration forms suitable for oral administration are those which function according to the state of the art and deliver OmpA or its derivatives of the invention in a rapid and/or modified way, for example, tablets (uncoated or coated tablets, for example with coatings which are resistant to gastric juice or dissolve slowly or are insoluble and which control the release of the compound of the invention), tablets which rapidly disintegrate in the mouth, or films/wafers, films/lyophilisates, capsules (for example hard or soft gelatin capsules), sugar-coated tablets, granules, pellets, powders, emulsions, suspensions, aerosols or solutions.

Parenteral administration includes intravenous drip or infusion, subcutaneous, intraperitoneal or intramuscular injection, pulmonary administration, e.g., by inhalation or insufflation, or intrathecal or intraventricular administration. Administration forms suitable for parenteral administration are, inter alia, injection and infusion preparations in the form of solutions, suspensions, emulsions, lyophilisates or sterile powders.

Oral or parenteral administration is preferred, especially oral and intravenous administration. Intravenous dosage is particularly preferred for example for the treatment of acute central nervous system infection.

OmpA or its derivatives used according to the invention can be converted into suitable pharmaceutical compositions. This can take place in a known manner by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and masking tastes and/or odors.

The administration form of the invention comprises 0.0001% to 10% by weight of OmpA or its derivatives, preferably 0.5% to 5% by weight of OmpA or its derivatives. The time of treatment with the pharmaceutical composition of the invention is determined on the basis of severity of the disease to be treated and the conditions of individual patients. A doctor shall determine the adequate amount of time of treatment with the pharmaceutical composition of the invention.

The invention also provides a method for vaccinating a mammal to produce an antibody against bacterial infection in central nervous system and/or peripheral blood circulation, which comprises administering to said mammal an effective amount of an outer membrane protein A or its derivatives. In view of the discovery that OmpA can treat and/or prevent and/or diagnose bacterial infection in central nervous system and/or peripheral blood circulation, OmpA was introduced to an animal for vaccination. It is found that OmpA can induce specific antibody production.

The antibodies of the invention can be produced by any method known in the art. Polyclonal antibodies to OmpA can be produced by various procedures well known in the art. For example, OmpA can be administered to various host animals including, but not limited to, rabbits, mice, rats, etc. to induce the production of sera containing polyclonal antibodies specific for OmpA. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Antibodies of the invention can be used to assay OmpA levels in a biological sample using classical serological and immunohistological methods as described herein or as known to those of skill in the art. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as glucose oxidase; radioisotopes, such as iodine ($^{125}$I, $^{121}$I), carbon ($^{14}$C), sulfur ($^{35}$S), tritium ($^{3}$H), indium ($^{12}$In), and technetium ($^{99}$Tc); luminescent labels, such as luminol; and fluorescent labels, such as fluorescein and rhodamine, and biotin.

The invention further provides a method of detecting or diagnosing bacterial infection in central nervous system and/or peripheral blood circulation in a mammal. In one embodiment, the detection or diagnosis comprises: coating a first specific anti-OmpA antibody onto a matrix surface (such as ELISA plates or magnetic nano-particles) that can immunospecifically bind to OmpA molecules in blood or OmpA on bacterial membranes, adding a sample from peripheral blood circulation and/or the central nervous system to the matrix, adding a second anti-OmpA antibody with a label, and detecting the binding of the anti-OmpA antibodies to the OmpA molecules or OmpA on bacterial membranes, wherein the binding result indicates that the mammal may suffer from the bacterial infections in the peripheral blood circulation and/or the central nervous system.

According to the invention, the first specific anti-OmpA antibody is coated onto the matrix surface using a method and commercial coating buffer known in the art and any appropriate matrix can be used in the method. The matrix is preferably ELISA plates or magnetic nano-particles. The anti-OmpA antibody can specifically bind to OmpA molecules in blood or OmpA on bacterial membranes. To allow the binding detectable, the anti-OmpA antibody specifically binding to OmpA molecules can be detected by using a second anti-OmpA antibody with a label. According to the invention, the term "label" refers to a molecule or moiety having a property or characteristic which is capable of detection. A label may be directly detectable, as with radioisotopes, fluorophores or chemilumiphores; or a label may be indirectly detectable, as with haptens or polynucleotide tails. When indirect labels are used for detection or signaling purposes, they are used in conjunction with a signaling entity complex. A "signaling entity" is a molecule or moiety which provides the detectable property or characteristic. The signaling entity may be direct, as with a colloidal particle (e.g. colloidal gold or selenium); or it may be indirect, as with an enzyme (e.g. alkaline phosphatase, beta.-galactosidase or horseradish peroxidase). Indirect signaling entities may require additional components, e.g. substrate, as is well known in the arm. The "signaling entity complex" includes a signaling entity conjugated to specific binding partner, such as an antibody or polynucleotide. Such conjugates may be prepared according to any known method of conjugation.

According to the invention, the binding of the anti-OmpA antibody to the OmpA molecule in peripheral blood or central nervous system can be used to detect the existence of the OmpA molecule. If the OmpA molecule exists in the peripheral blood or central nervous system of a subject, it represents that the subject may be infected by a bacteria with OmpA molecule.

EXAMPLE

The following examples illustrate the invention. The invention is not restricted to the example.

Example 1

Adhesion and Invasion Assay

For total C6 glioma cell-associated bacteria studies, confluent cell monolayers were incubated with respective bacteria strain E. coli E44, E91 and MG1655 at indicated time intervals at 37° C. E. coli E44 is a K1 strain RE218 (O18:K1: H7) and derived from a cerebrospinal fluid of a neonate with meningitis. E. coli E91 is a mutant lacking the entire OmpA gene and generated from strain E44. E. coli MG1655 is a nonpathogenic strain and non-invasive in blood brain barrier, so it was used as a control.

In the adhesion assay, the C6 glioma cells were infected with the above-mentioned bacteria strains (MOI (bacteria-to-cell ratio)=10) at indicated time intervals. The C6 glioma cell monolayers were then washed with culture medium three times and lysed in 0.5% Triton X-100. The released bacteria were enumerated by plating on sheep blood agar plates. As shown in the results of the adhesion assay (FIG. 1), the numbers of E. coli E44 largely increases over time. However, the numbers of E. coli E91 and MG1655 are smaller than E. coli E44.

Figure 2:
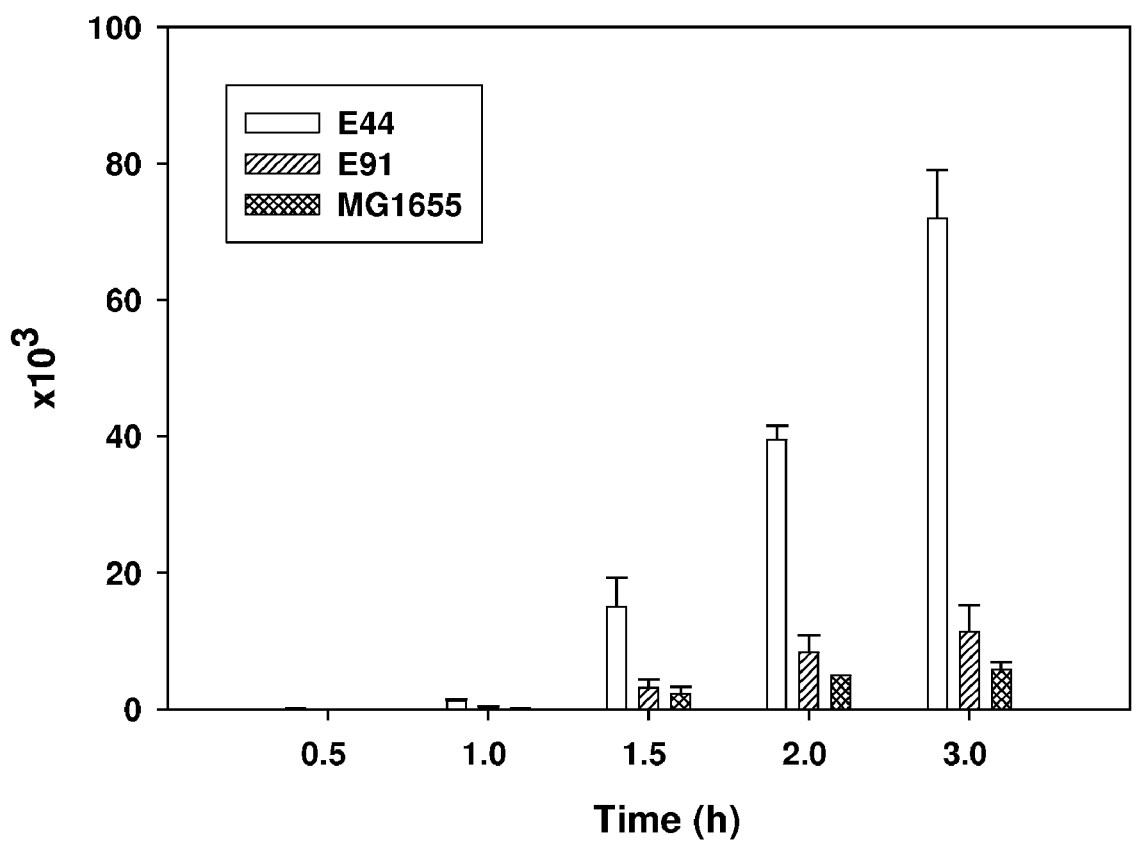
FIG. 2 shows the time course of *E. coli* strain invasion.
Figure 3:
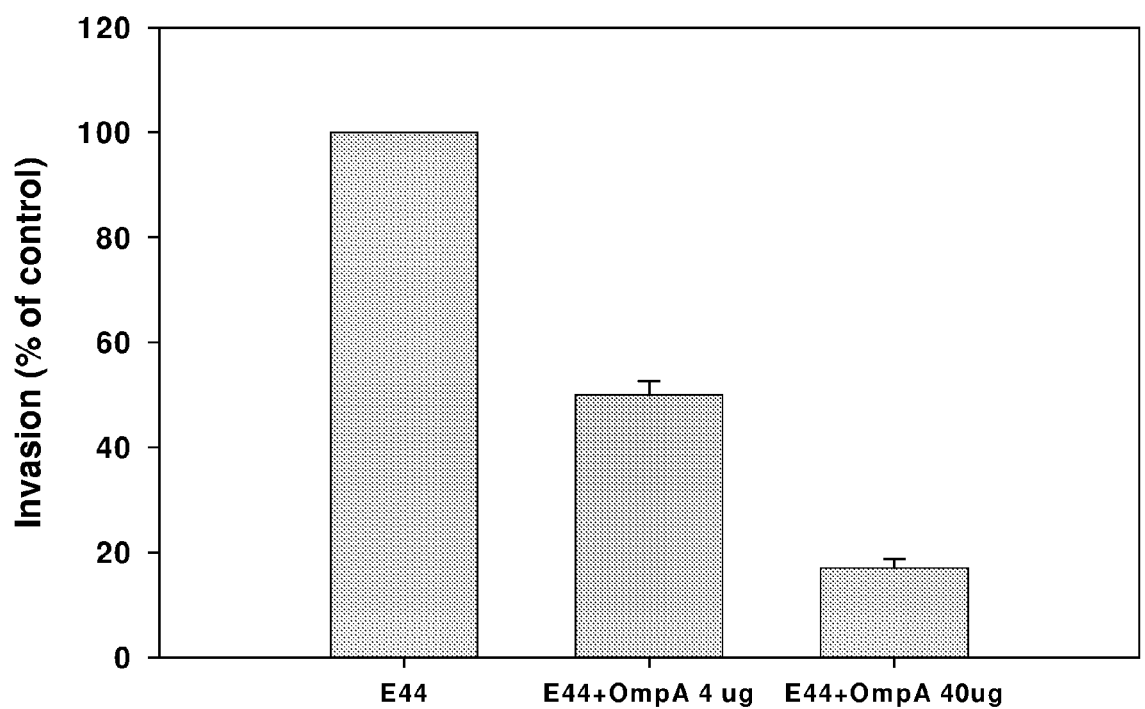
FIG. 3 shows the inhibition of *E. coli* E 44 invasion into C6 glioma cells by OmpA.

In the invasion assay (gentamicin protection assay), for intracellular bacteria studies, the glioma C6 confluent cell monolayers were incubated with the above-mentioned bacteria strain (MOI=10) at indicated time intervals at 37° C. The monolayers were then washed with culture medium three times and further incubated with culture medium containing gentamicin (100 μg ml$^{-1}$) for 2 hours to kill extracellular bacteria. The monolayers were washed three times again and lysed in 0.5% Triton X-100. The released bacteria were enumerated by plating on sheep blood agar plates. As shown in FIG. 2 for the invasion assay, the numbers of E. coli E44 are much larger than those of E. coli E91 and MG1655. In the invasion inhibition assay, the glioma C6 confluent cell monolayers were infected with E. coli E44 (MOI=10) with 4 μg or 40 μg OmpA for 2 hours. The monolayers were then washed with culture medium three times and further incubated with culture medium containing gentamicin (100 μg ml$^{-1}$) for 2 hours to kill extracellular bacteria. The released bacteria were enumerated by plating on sheep blood agar plates. As shown in FIG. 3, the mixtures of E. coli E44 and OmpA indeed inhibit the invasion of E. coli E44. OmpA can inhibit more than 55% (4 μg) and 80% (40 μg) invasion of E. coli E44.

Example 2

Animal Experiments

C57BL/6 mice were obtained from the National Laboratory Animal Center of Taiwan, and kept under pathogen-free conditions. Animal procedures were performed in accordance with the institutional protocol of Taipei Medical University under an approved protocol.

Figure 4:
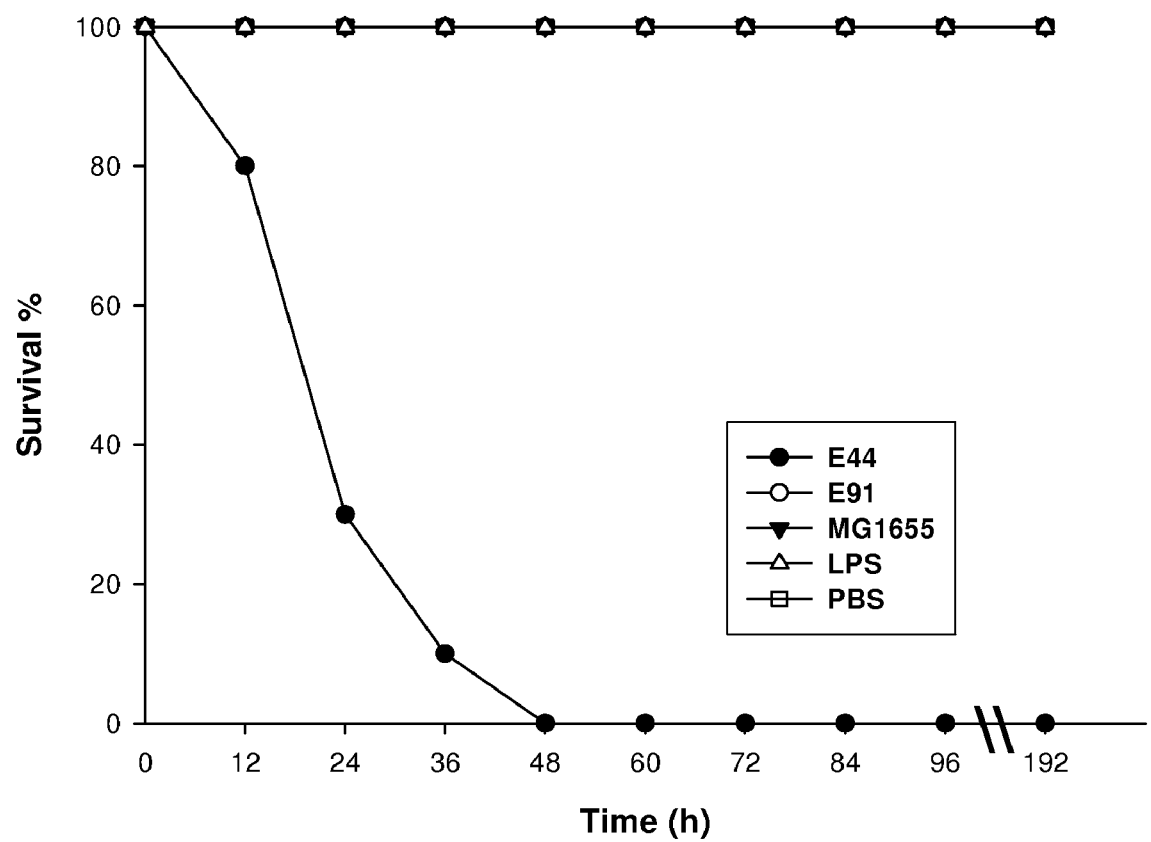
FIG. 4 shows the survival of C57BL/6 mice intracerebrally injected with *E. coli* strains.

8-12 week-old C57BL/6 mice were randomly divided in groups. Each group contained 5 to 10 mice. Mice were anesthetized with pentobarbital sodium salt (50 mg kg$^{-1}$) by intraperitoneal injection, and then each mouse was infected with $5 \times 10^5$ E. coli strains E44, E91, or MG1655 in 20 μl PBS, or 5 μg LPS in 20 μl PBS by intracerebral injection. 20 μl PBS was used as a control treatment. Survival in C57BL/6 mice after E. coli strains infection was assessed 8 days postadministration. As shown in FIG. 4, all of the mice infected with E. Coli E44 died after 2 days.

Figure 5:
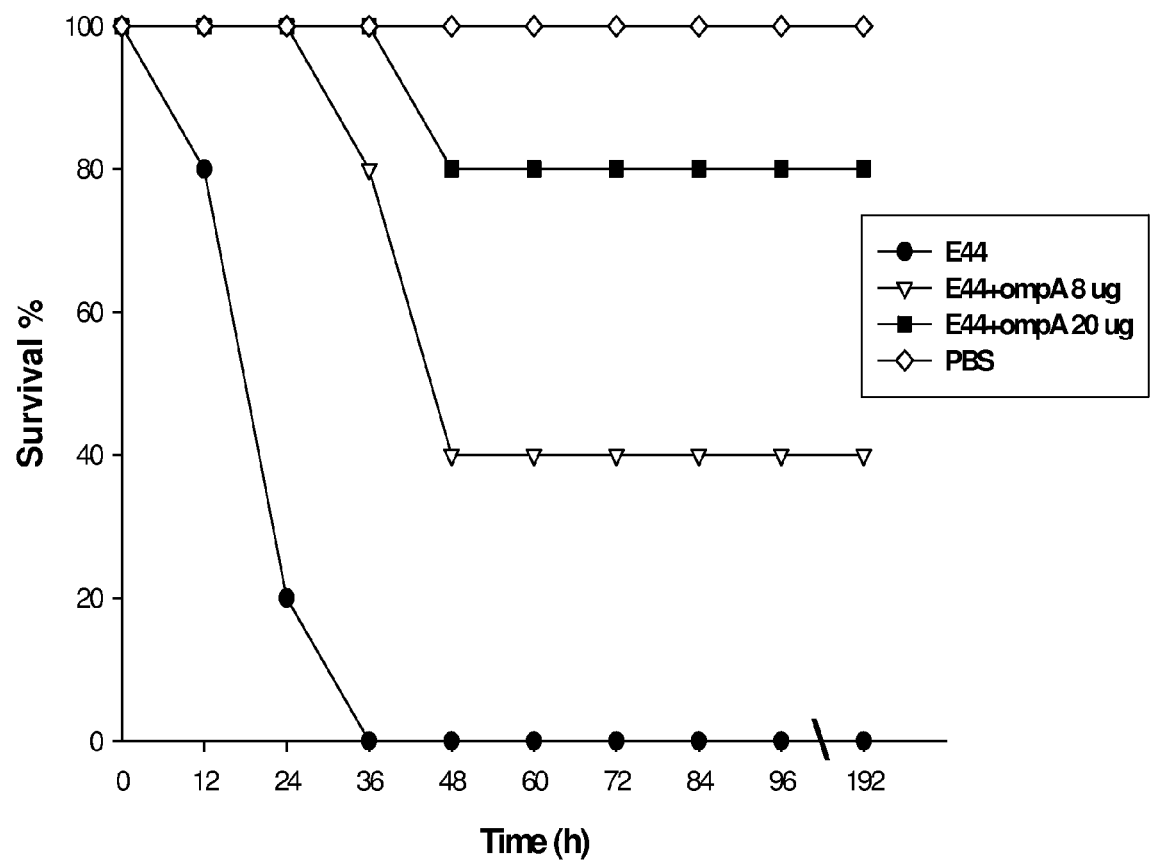
FIG. 5 shows that OmpA prolongs the survival of the mice intracerebrally injected with *E. coli* E44.

To investigate the role of recombinant OmpA in the survival of C57BL/6 mice following intracerebral E44 administration, 8-12 weeks-old C57BL/6 mice were anesthetized with pentobarbital sodium salt (50 mg kg$^{-1}$) by intraperitoneal injection. Then each mouse was infected with E44 $5 \times 10^5$ in 20 μl PBS, without or with premixed with 8 μg or 20 μg recombinant OmpA, by intracerebral injection. PBS 30 μl was used as a control treatment. Survival in C57BL/6 mice was assessed 8 days postadministration. FIG. 5 showed that OmpA prolongs the survival of the mice intracerebrally injected with E. coli E44. Around 40% and 80% of the mice survived in E. coli E44 with 8 μg OmpA and E. coli E44 with 20 μg OmpA.

Example 3

Immunocytochemistry

Figure 6:
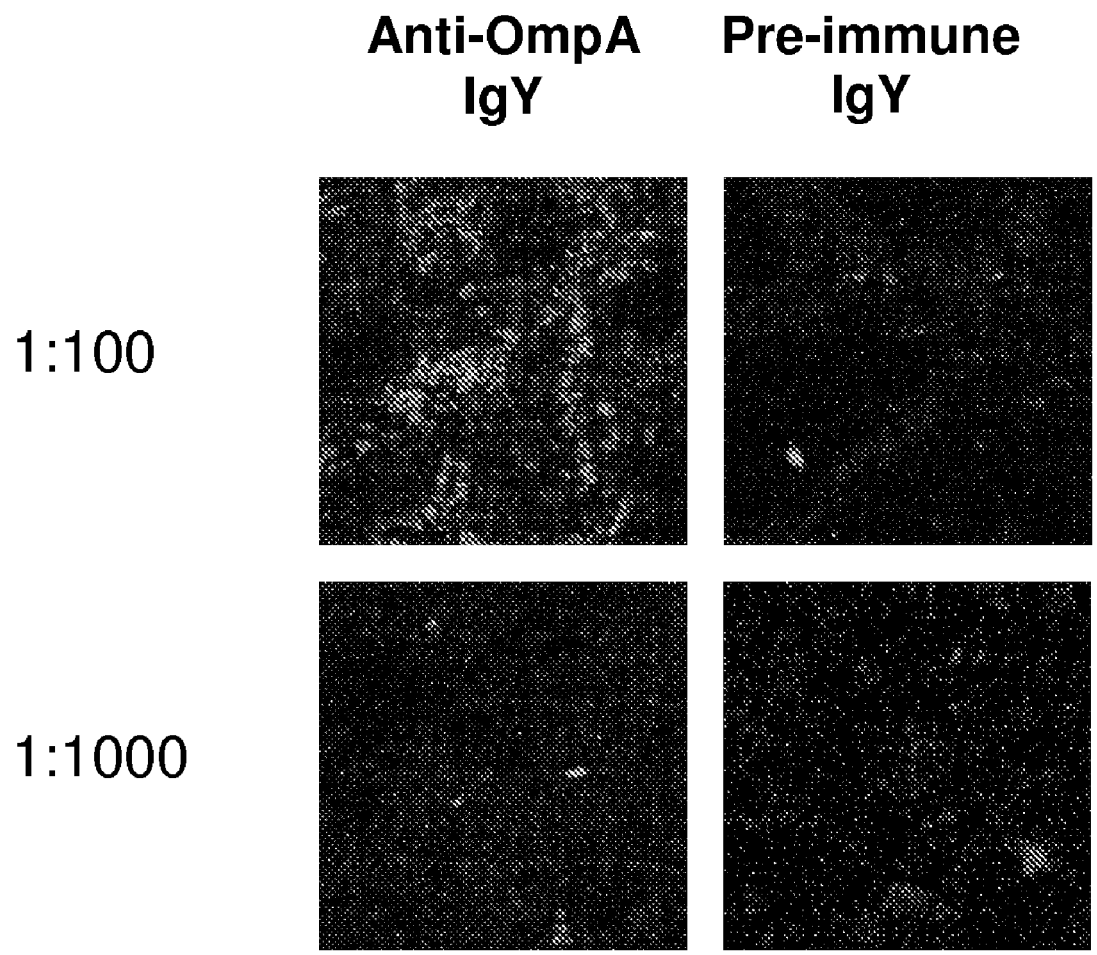
FIG. 6 shows the binding of anti-OmpA IgY antibodies to *E. coli* E44 using Confocal Spectral Microscope Imaging System.

C6 glioma cell monolayers were infected with E. Coli and fixed with 4% paraformaldehyde. The resulting C6 cell samples were blocked with 1% BSA and then incubated with a solution containing polyclonal chicken anti-OmpA IgY Ab (diluted 1:100 and 1:1000) from chicken so that the anti-OmpA IgY Ab can bind to the OmpA of E. Coli.. Polyclonal IgY Ab from non-immunized chicken was used as a negative control. Finally, samples were incubated with FITC-labeled anti-IgY secondary antibody (diluted 1:500). Slides were mounted in 50% glycerol-PBS, and then examined with TCS SP5 Confocal Spectral Microscope Imaging System (Leica). FIG. 6 showed that the anti-OmpA antibodies produced clearly bind to E44, whereas IgY from non-immunized chicken did not show any binding activity.

Example 4

Immunization Assay

Figure 7:
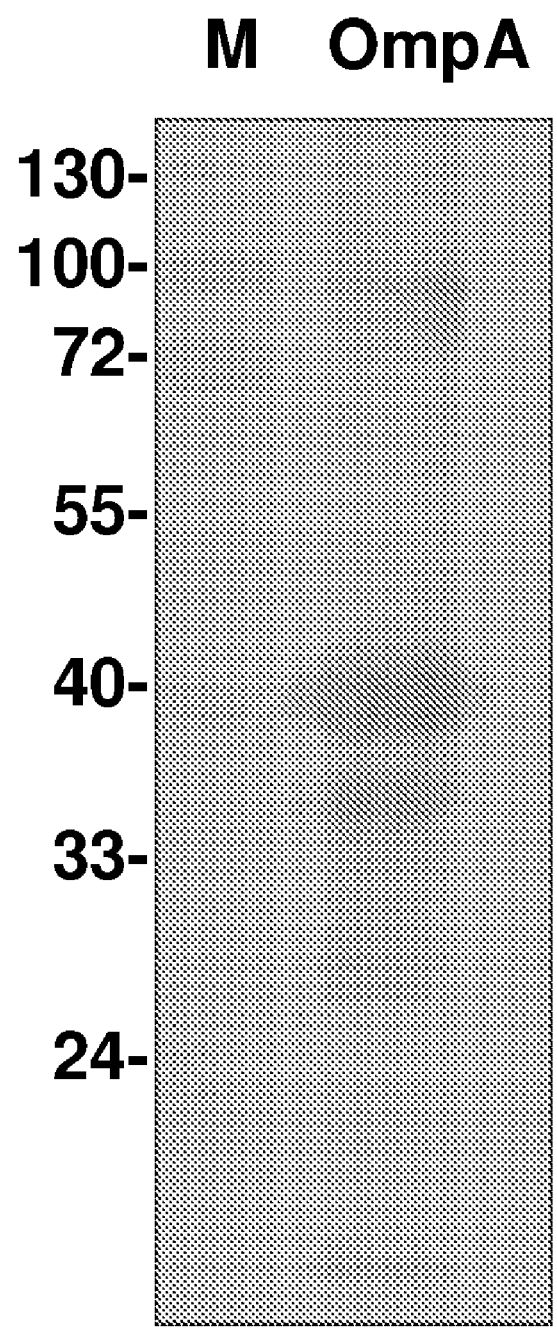
FIG. 7 shows the electrophoresis plot of the antibody against OmpA.

C57BL/6 mice used in this assay are the same as those in Example 2. At the first week, the mice were immunized with 30 μg OmpA with complete Freund's adjuvant as the first immunization. At the second week, 30 μg OmpA with incomplete Freund's adjuvant as the second immunization. At the third week, 30 μg OmpA with incomplete Freund's adjuvant as the third immunization. At the fourth week, 30 μg OmpA with incomplete Freund's adjuvant as the fourth immunization. Thereafter, the polyclonal antibodies from the immunized mice were isolated and used to detect the OmpA molecule immobilized on the nitrocellulose paper. FIG. 7 showed that OmpA molecule can be detected using the polyclonal antibodies elicited in the mice in a western blot analysis.

What is claimed is:

1. A method for the treatment of *Escherichia coli* infection in central nervous system and/or peripheral blood circulation in a mammal, which comprises administering to said mammal an effective amount of an outer membrane protein A (OmpA) of *Escherichia coli*.

2. The method of claim 1, wherein the mammal is human.

3. The method of claim 1, wherein the OmpA is a recombinant OmpA.

4. The method according to claim 1, wherein the OmpA is administrated orally or via intravenous injection.

5. The method according to claim 1, wherein the OmpA is administrated at an amount of 0.0001% to 10% by weight of OmpA.

6. The method according to claim 1, wherein the OmpA is administrated at an amount of 0.5% to 5% by weight of OmpA.

7. A method for vaccinating a mammal to produce an antibody against *Escherichia coli* infection in central nervous system and/or peripheral blood circulation, which comprises administering to said mammal an effective amount of an OmpA of *Escherichia coli*.

8. The method of claim 7, wherein the antibody is a polyclonal antibody.

9. The method of claim 7, wherein the mammal is human.

10. The method of claim 7, wherein the OmpA is a recombinant OmpA.

11. The method according to claim 7, wherein the OmpA is administrated at an amount of 0.0001% to 10% by weight of OmpA.

12. The method according to claim 7, wherein the OmpA is administrated at an amount of 0.5% to 5% by weight of OmpA.

* * * * *